(12) United States Patent
Nasralla (10) Patent No.: US 10,368,932 B2
(45) Date of Patent: Aug. 6, 2019

(54) KYPHOPLASTY DEVICE AND METHOD (71) Applicant: Pan Medical US Corporation, Largo, FL (US)

(72) Inventor: Max Nasralla, Gloucester (GB)

(73) Assignee: PAN MEDICAL US CORPORATION, Largo, FL (US)

( * ) Notice: Subject to any disclaimer, the term of this patent is extended or adjusted under 35 U.S.C. 154(b) by 0 days.

(21) Appl. No.: 16/271,343

(22) Filed: Feb. 8, 2019

(65) Prior Publication Data
US 2019/0167327 A1 Jun. 6, 2019

Related U.S. Application Data (63) Continuation of application No. PCT/US2018/034488, filed on May 24, 2018.

(60) Provisional application No. 62/511,685, filed on May 26, 2017.

(51) Int. Cl.
*A61B 17/88* (2006.01)
(52) U.S. Cl.
CPC ................ *A61B 17/8855* (2013.01)
(58) Field of Classification Search
CPC ... A61B 17/88; A61B 17/885; A61B 17/8852; A61B 17/8855; A61B 17/8858
See application file for complete search history.

(56) References Cited

U.S. PATENT DOCUMENTS

2003/0191452 A1* 10/2003 Meglin ................ A61M 27/00 604/537
2004/0092946 A1* 5/2004 Bagga .................. A61B 17/16 606/93
2007/0010844 A1 1/2007 Gong et al.
2007/0066987 A1 3/2007 Scanlan et al.
2009/0131867 A1* 5/2009 Liu ..................... A61B 17/8811 604/96.01
2010/0298832 A1* 11/2010 Lau ..................... A61B 17/1642 606/80
2011/0196499 A1* 8/2011 Boucher ............ A61B 17/1631 623/17.16
2011/0264099 A1 10/2011 Quinto
2012/0004594 A1 1/2012 Schulz et al.
2012/0197319 A1 8/2012 Auyoung et al.
2013/0165942 A1* 6/2013 Tan-Malecki ...... A61B 17/8855 606/94

(Continued)

OTHER PUBLICATIONS

International Search Report and Written Opinion issued in counterpart PCT Application No. PCT/US2018/034488 dated Aug. 27, 2018 (seven (7) pages).

*Primary Examiner* — Eric S Gibson
(74) *Attorney, Agent, or Firm* — Olive Law Group, PLLC (57) ABSTRACT A kyphoplasty device and method offers access and serves as a channel to radially locate sites in the vertebral body using a curved needle made of a material, such as nitinol, which recovers its shape after passing through a straight cannula. The needle serves as a channel facilitating precise positioning of an inflatable bone tamp. The bone tamp creates a void when inflated at the proper location within a nonlinear, arcuate-shaped channel defined by the shape of the needle within the vertebral body. After the bone tamp is deflated and removed, the needle serves as a conduit for delivery of cement into the cavity formed by the bone tamp, without repositioning the needle.

13 Claims, 13 Drawing Sheets

(56) References Cited

U.S. PATENT DOCUMENTS

| | | | | |
|---|---|---|---|---|
| 2013/0197563 A1* | 8/2013 | Saab | ............... | A61M 29/02 |
| | | | | 606/191 |
| 2013/0345709 A1* | 12/2013 | Burger | ............... | A61B 17/8811 |
| | | | | 606/94 |
| 2013/0345765 A1* | 12/2013 | Brockman | ......... | A61B 17/8855 |
| | | | | 606/86 R |
| 2014/0005711 A1* | 1/2014 | Saab | ................. | A61M 25/0144 |
| | | | | 606/191 |
| 2016/0051306 A1* | 2/2016 | Sasaki | ................ | A61B 17/8811 |
| | | | | 606/93 |

\* cited by examiner

KYPHOPLASTY DEVICE AND METHOD

CROSS RELATED APPLICATIONS

This application claims priority to PCT/US1834488 filed May 24, 2018 which claims priority to U.S. Provisional Appl. No. 62/511,685 filed May 26, 2017, both of which are hereby incorporated by reference herein in their entireties.

FIELD OF THE INVENTION

The field relates to spinal kyphoplasty procedures and devices used for such procedures.

BACKGROUND

Spinal kyphoplasty procedures are known. These procedures stabilize or reverse painful vertebral compression fractures in lumbar or thoracic regions of the vertebral column. Other treatments are known but are more focused on the alleviation of symptoms with analgesic medication and spinal support. Kyphoplasty is a surgical procedure intended for patients whose condition is refractory to medical therapy and in whom there is continued vertebral collapse. Kyphoplasty procedures are considered a relatively low risk compared to other surgical procedures. Typically, bone access tools are used to create/drill a channel to a fracture in the vertebral column. Then, one or a pair of inflatable bone tamps are inserted through a straight cannula into an appropriate site or sites under fluoroscopic guidance to position the bone tamp or tamps at a proper location before being inflated with a liquid contrast medium via an inflation device. The inflation may relieve pressure caused by vertebral collapse or fracture. The bone tamp is deflated and carefully withdrawn from the channel while keeping the vertebral collapse or fracture from recollapsing or returning to its prior position. Then, the cavity created by the bone tamp is filled by a bone cement delivered by cement delivery tooling, again, under fluoroscopic observation. This often requires trial and error with the fluoroscope being brought in and removed repeatedly, interrupting and delaying the procedure. Once positioned and injected into the cavity, the bone cement hardens, stabilizing and reinforcing the vertebral body structure.

SUMMARY

A kyphoplasty device comprises a cannula, such as a ten gauge, straight, direct working cannula with a diamond tip stylet, a needle having an arcuate end portion that is flexible enough to be inserted through the channel provided by the straight cannula and resilient enough to return to its arcuate shape upon exiting the straight channel provided through the cannula; and an inflatable bone tamp configured to be inserted through the needle to the precise location where the bone tamp is needed to stabilize or reverse the compression caused by the vertebral collapse or fracture. The cannula may be designed and adapted to advance through hard bone of the vertebral column in a surgical procedure to access a collapsed portion or fracture within a vertebral body. The needle is arranged with a distal end to be inserted through the cannula. The distal end is configured to have a resilient arcuate shape made of a material capable of straightening sufficiently to pass through the cannula and resilient enough that it returns to its former, arcuate shape as it exits the cannula. For example, a nitinol needle may be used. The inflatable bone tamp is sized to fit through the needle such that the inflatable bone tamp extends from the end of the needle at a location inaccessible by a straight cannula. This allows a single bone tamp to be used to apply pressure at the precise location to cause the vertebral body to be stabilized and/or restored to a position that relieves pressure on nerves. The device may-include a bone cement delivery device configured to mate with the needle for delivery of bone cement from the bone cement delivery device, through the needle, such that the arcuate, distal end of the needle delivers the bone cement precisely to the location of the cavity formed by the bone tamp, which is removed from the needle prior to insertion of the bone cement through the needle.

In one example, a ten gauge direct working cannula with a diamond tip stylet is adapted to allow a bevel tip stylet to be inserted/substituted within the cannula, if a bevel tip is considered suitable for the procedure instead of a diamond tip stylet. For example, a nitinol needle is adapted to be inserted into the direct/straight working cannula and has a curved distal end that resiliently returns to its curved shape as it exits the straight cannula, and the nitinol needle is configured to have an inner channel sized to receive an inflatable bone tamp. The size of the internal channel through the ten gauge cannula, the size of the channel through the needle and the size of the shaft and balloon of the bone tamp must be arranged such that the cannula is adapted to fit through a pedicle of the vertebral body to access a region of the vertebral body near the cortical rim that is inaccessible to a straight cannula. Thus, a substantially arcuately shaped nitinol needle is essential to provide access to the precise location needed for the bone tamp to provide the proper cavity on the reverse side of the spinal column for the bone cement to be able to stabilize the vertebral body through a single pedicle. For example, a length of a thirteen gauge shaft of an inflatable bone tamp is elongated in order for the shaft of the bone tamp to extend the inflatable bone tamp from the distal end of the needle. This specially designed bone tamp has a length and shaft diameter capable of being inserted precisely through the needle and to the precise location where a cavity is to be created to stabilize the vertebral body. This location is inaccessible to a straight cannula. The void or cavity may be filled with a bone cement. For example, the needle, which is already located at the proper position is utilized for insertion of the bone cement after the inflatable bone tamp is carefully deflated and removed from the needle. In one example, a digital inflation device is provided for inflating and deflating the inflatable bone tamp in order to achieve the desired void or cavity for the bone cement.

In one example, a thirteen gauge inflatable bone tamp has a length selected such that the entire inflatable portion of the bone tamp extends from the needle a precise distance when the bone tamp is fully inserted through the shaft of the needle. The shaft of the needle is selected to have an inner diameter greater than the largest outer diameter of the bone tamp shaft and inflatable portion of the bone tamp and an outer diameter selected to fit through the shaft of a ten gauge cannula. Also, the material of the needle and the wall thickness are selected to provide a needle with a distal arcuate end flexible enough to fit through the shaft of the cannula and resilient and stiff enough to return to its original shape while exiting from the end of the shaft of the cannula. For example, once the cannula is properly positioned, the positioning of the needle and balloon is greatly simplified compared to any known device and method. Two radiopaque markers may be disposed at an interior portion of the shaft within the balloon to increase radiopacity underfluoroscopy/imaging during a procedure. In one example, two markers are disposed on an inflatable bone tamp shaft using a microscopic refractory light. Unlike known devices, a nitinol needle disposed through the cannula has an arcuate distal end and is adapted for delivering bone cement through the needle to the void/cavity site created by inflation of the inflatable bone tamp after the inflatable bone tamp is removed from the needle.

A method of using a kyphoplasty device may comprise any and/or all of the following steps: advancing a direct, straight working cannula with a stylet through the compact bone to access the cancellous bone/vertebral body through a single pedicle; withdrawing the stylet from the cannula once a desired depth within the bone is reached; introducing an arcuate distal end of a needle, such as a nitinol needle, through the straight working cannula to further clear out any bone tissue and preparing the site for the precise placement of an inflatable bone tamp; withdrawing the curved nitinol needle, such as up to 15 millimeters; withdrawing a core from the shaft of the needle; introducing the inflatable bone tamp, such as a thirteen gauge bone tamp, through the needle and positioning the bone tamp at the precise location and into the channel prepared by the nitinol needle; inflating the bone tamp to achieve a desired void and/or lift, creating a void/cavity at the location of the bone tamp; deflating the bone tamp and removing the bone tamp from the needle; and delivering bone cement through the needle to the location of the void/cavity. In one example, the needle has a removable core that fills the channel through the needle during insertion of the needle, and the core blocks any debris from clogging the needle. For example, the core is removed prior to inserting the bone tamp.

A kyphoplasty device may comprise a cannula having a straight channel, the channel being of no greater than ten gauge, the channel being defined by a cylindrical wall, and the channel having a distal end at a length of at least thirty millimeters from a proximal end; a needle having a length at least ten millimeters longer than the length of the channel of the cannula, and the needle having an arcuate end portion made of a material that has a flexibility and size selected such that the needle is insertable through the straight channel of the cannula, and the needle has a resiliency selected such that the arcuate end portion of the needle returns to an arcuate shape of the arcuate end portion upon exiting the channel of the cannula; and an inflatable bone tamp having an outer diameter, when deflated, such that the bone tamp is insertable through the needle to a precise location where the bone tamp is needed to stabilize or reverse compression caused by vertebral collapse or fracture of vertebral bone structures, the vertebral bone structures not being any portion of the device. For example, the cannula is adapted to advance through hard bone of the vertebral bone structures. The material of the needle may be of nitinol.

A reservoir of bone cement and the needle may be configured for coupling the reservoir with the needle for delivery of the bone cement contained in the reservoir through the needle, after the bone tamp is removed from the needle, such that the arcuate end of the needle delivers the bone cement precisely to the location of a cavity formed in the vertebral bone structures by the bone tamp, when the bone tamp is inserted through the needle and is inflated.

A diamond tip stylet may be inserted through the channel of the cannula. A bevel tip stylet may be inserted through the channel of the cannula. In one example, a bevel tip stylet suitable is used for insertion through the channel of the cannula when the diamond tip stylet is removed from the channel of the cannula.

The cannula is adapted to fit through a pedicle of the vertebral bone structures, for example, and the arcuate portion of the needle accesses a region of the vertebral body near the cortical rim of the vertebral bone structures that is inaccessible to the cannula. For example, the bone tamp has a thirteen gauge shaft and the bone tamp extends through the needle. The size, shape and length of the bone tamp and of the cannula matters. No previous system has been able to so precisely place a balloon catheter bone tamp at this specific location in the spinal structures to achieve the desired results. Two radiopaque markers may be disposed at an interior portion of the bone tamp within the balloon to increase radiopacity under fluoroscopy for confirming precise placement of the bone tamp. In one example, a removable core, wherein the removable core is inserted through the needle during insertion of the needle through the cannula and into the vertebral bone structures, such that the removable core blocks any debris from clogging the needle.

For example, a method of using the medical device comprises the steps of inserting a stylet through the cannula; advancing the stylet and cannula through a pedicle of the vertebral bone structures to a location near a region of a cortical rim of the vertebral bone structures; inserting the needle through the cannula such that the arcuate end portion extends into the region of the cortical rim that is otherwise inaccessible by the cannula; inserting the inflatable bone tamp through the needle into the region of the cortical rim; inflating the bone tamp; removing the bone tamp from the needle; coupling a reservoir of bone cement to the needle; injecting bone cement from the reservoir, through the needle, and into the region of the cortical rim. In one example, a removable core is removed from the needle after the needle is inserted into the region of the cortical rim and before inserting the inflatable bone tamp through the needle.

BRIEF DESCRIPTION OF THE DRAWINGS

The following drawings are illustrative examples and do not further limit any claims that may eventually issue.

When the same reference characters are used, these labels refer to similar parts in the examples illustrated in the drawings.

DETAILED DESCRIPTION

Figure 1A:
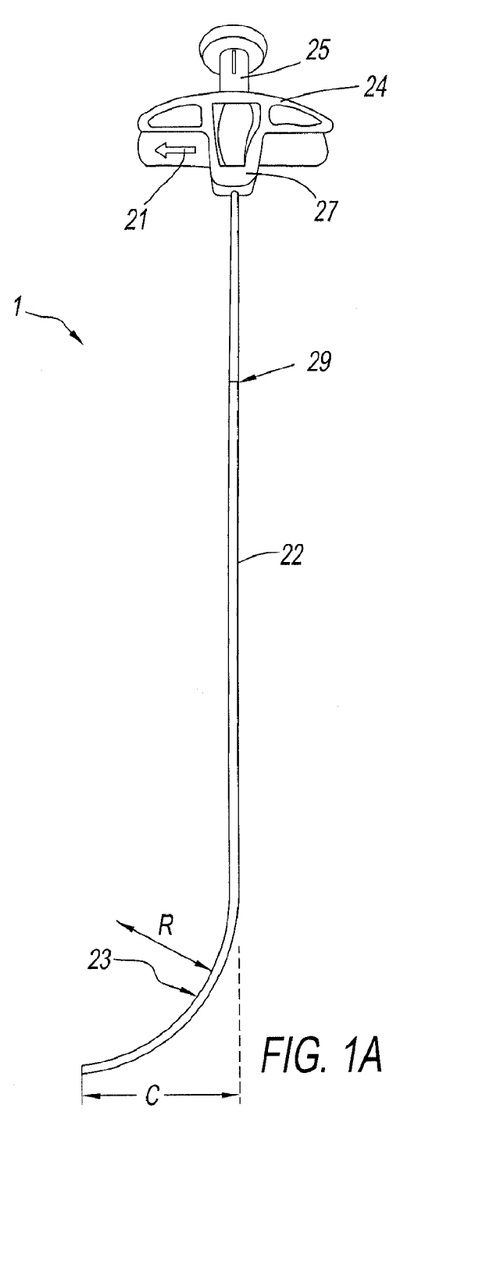
FIG. 1A illustrates an example of a needle assembly of a kyphoplasty device, the needle having an arcuate distal end.
Figure 1B:
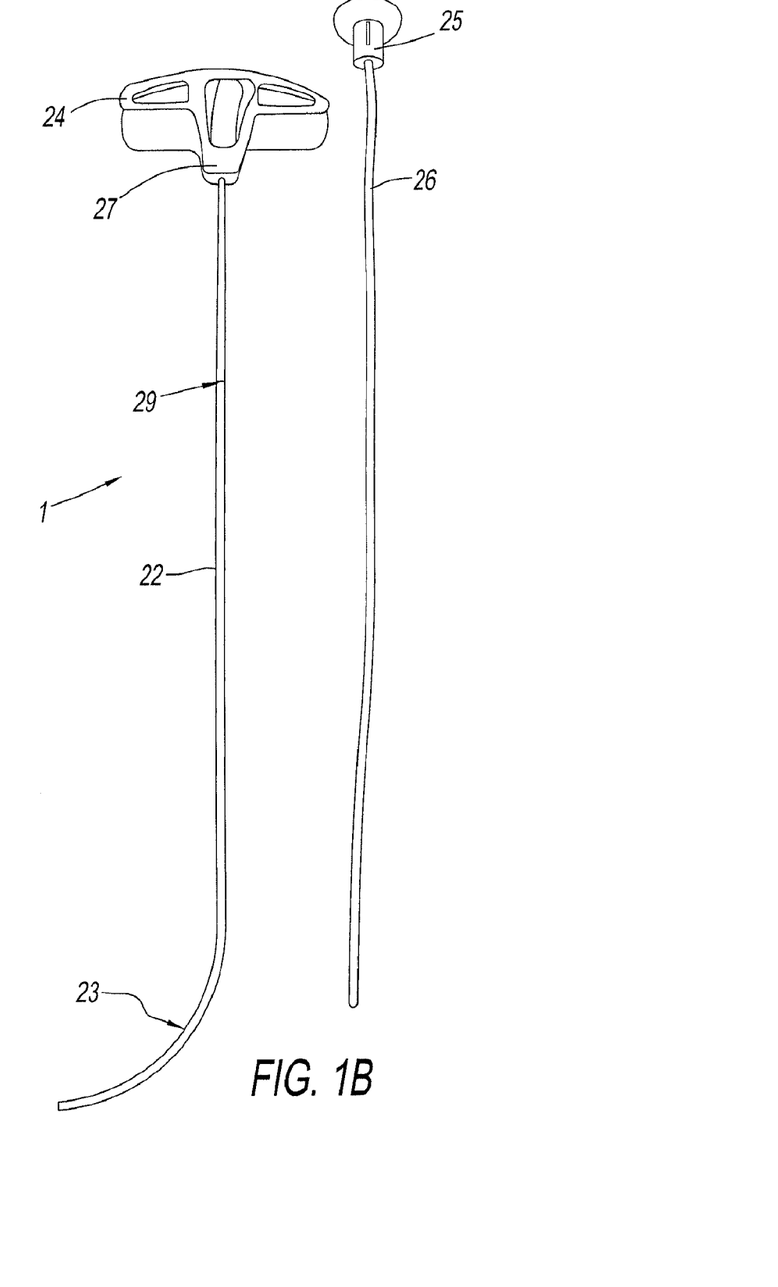
FIG. 1B illustrates an example of a partially disassembled view of the needle assembly of FIG. 1A.

An example of a kyphoplasty device comprises a needle assembly 1, a cannula 2, and an inflatable bone tamp 11. The needle 22 of the needle assembly 1 is configured to fit through the shaft 32 of the cannula 2. For example, the cannula 2 may comprise a ten gauge shaft 32, and the needle 22 is sized to fit through the ten gauge shaft 32. An example of a needle assembly 1 is illustrated in FIGS. 1A and 1B. The needle 22, such as a nitinol needle, includes an arcuate distal end 23 and a witness mark 29 disposed along a length of the shaft of the needle 22. The witness mark 29 is a visual cue for determining the position of the distal arcuate end 23 in relation to the cannula 2, for example. A grip 24, such as a plastic grip, is shown that comprises a transition portion that couples the handle 24 to the shaft of the needle 22. A removable knob 25 is attached to a core 26, and the core 26 is fit down the length of the tubular needle 22 to the end of the arcuate distal end 23, for example, as shown in the partially disassembled view of FIG. 1B. The core 26 may be configured to block debris from entering the needle 22, while the needle 22 is inserted through the shaft 32 of the cannula 2 and as the needle 22 extends into the vertebral body 42 as illustrated in the example shown in FIG. 3B. The distal arcuate end 23 is configured to be sufficiently flexible, allowing the arcuate end 23 to fit through the straight shaft 32 of the cannula 2, while remaining sufficiently rigid and resilient to return to its prior arcuate shape upon exiting the distal end of the shaft 32 and to push through cancellous bone within the vertebral body, for example. In one example, the configuration is selected for a needle made of nitinol having a distal arcuate end with a radius of curvature R of about 30 millimeters, the distal tip extending a distance C of 29 millimeters from a line extending along the surface of the tubular needle opposite of the tip, a length of the needle 22 measured as a straight line along the surface of the tubular needle opposite of the tip of 221 millimeters, and a wall having an inner diameter of 1.9 millimeters and an outer diameter of 2.4 millimeters, for example. The inflatable bone tamp 11 may be configured to fit through the 1.9 millimeter inner diameter of the needle 22, for example. In this example the wall thickness of the needle 22 is 0.5 millimeters. A directional indicator 21 may be used in combination with the witness mark 29 to indicate proper positioning of the needle 22 within the vertebral body 42, for example.

Figure 2:
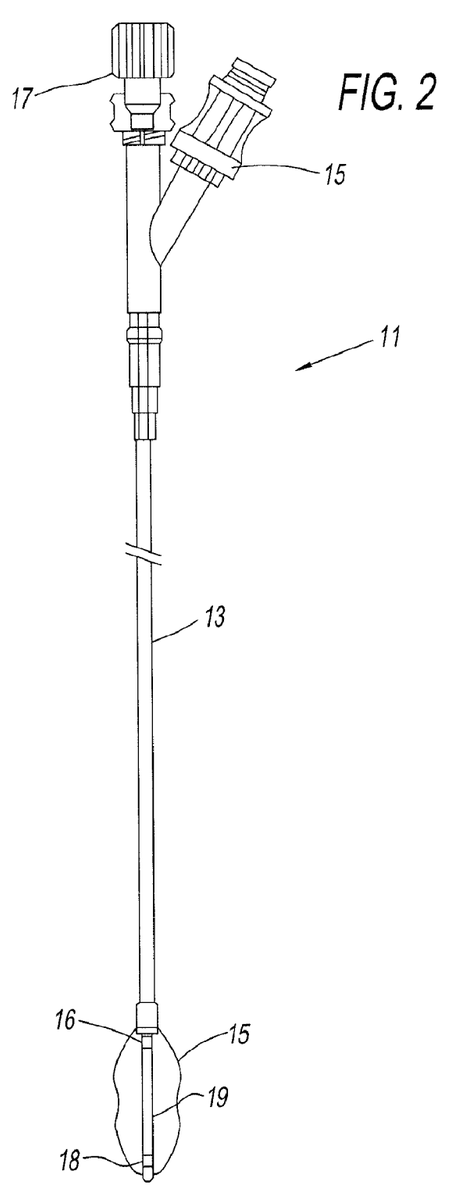
FIG. 2 illustrates an example of an inflatable bone tamp of a kyphoplasty device.

FIG. 2 illustrates an example of an inflatable bone tamp 11 with a shaft that is configured to fit through the needle 22 of the needle assembly 1. For example, the bone tamp 11 may include a thirteen gauge (1.83 mm) shaft. The length of the bone tamp 11 is selected to position the bone tamp 11 at a precise location within an anterior region of the vertebral body 42, which is inaccessible to a direct, straight cannula, as explained in more detail later, for example. In the example of FIG. 2, which has a portion of the length removed to fit the bone tamp 11 on the page, the inflatable bone tamp 11 is shown with a balloon 15 that is partially inflated. A pair of radiopaque markers 16, 18 are shown on an inner metallic shaft 19, for example, which aid in verifying the precise positioning of the balloon 15 within the vertebral body 42, for example. In one example, the radiopaque markers 16, 18 are platinum and/or iridium marker bands. The bone tamp 11 has a cap 17 on a proximal end of the bone tamp 11 and an inflation port 15 disposed near the proximal end for inflating and deflating the balloon 15. A lumen through the shaft 13 fluidically couples the inflation port 15 with the balloon 15. In one example, a digital inflation device (not shown) may be attached to the inflation port 15 for inflating and deflating the balloon 15. The balloon 15 may be of a polyurethane, for example.

Figure 3A:
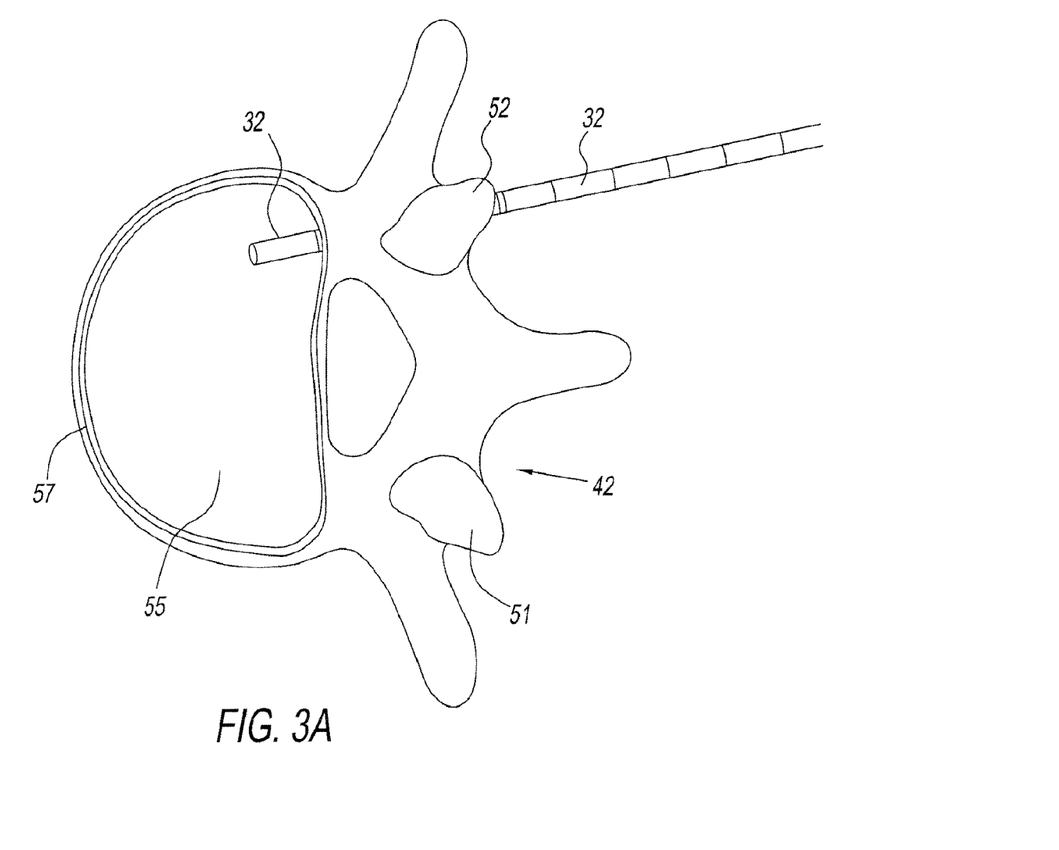
FIGS. 3A-3H illustrate examples of partial cutaway views of a collapsed vertebral body being stabilized by Kyphoplasty using an example of a kyphoplasty device.

FIGS. 3A-3H illustrate a method of kyphoplasty utilizing a kyphoplasty device. Kyphoplasty may be performed under a local anesthesia and/or a light sedative, while other surgical procedures may be required to use general anesthesia. After the anesthetic takes effect, a small incision may be made in the skin near the spine using a scalpel. The cannula 2 may be inserted percutaneously through the skin and soft tissues with torquing the cannula 2. When the cannula 2 meets solid bone, such as the left pedicle 51 or the right pedicle 52, torque may be used to insert the cannula through the hard bone. The cannula may be guided along the pedicle until it reaches cancellous bone within the vertebral body 42 using fluoroscopy, for example. Once the desired depth is reached and the distal tip of the cannula 2 has been positioned in a desired location, the stylet 34 may be removed from the cannula 2, as illustrated in FIG. 3A, for example.

Figure 3B:
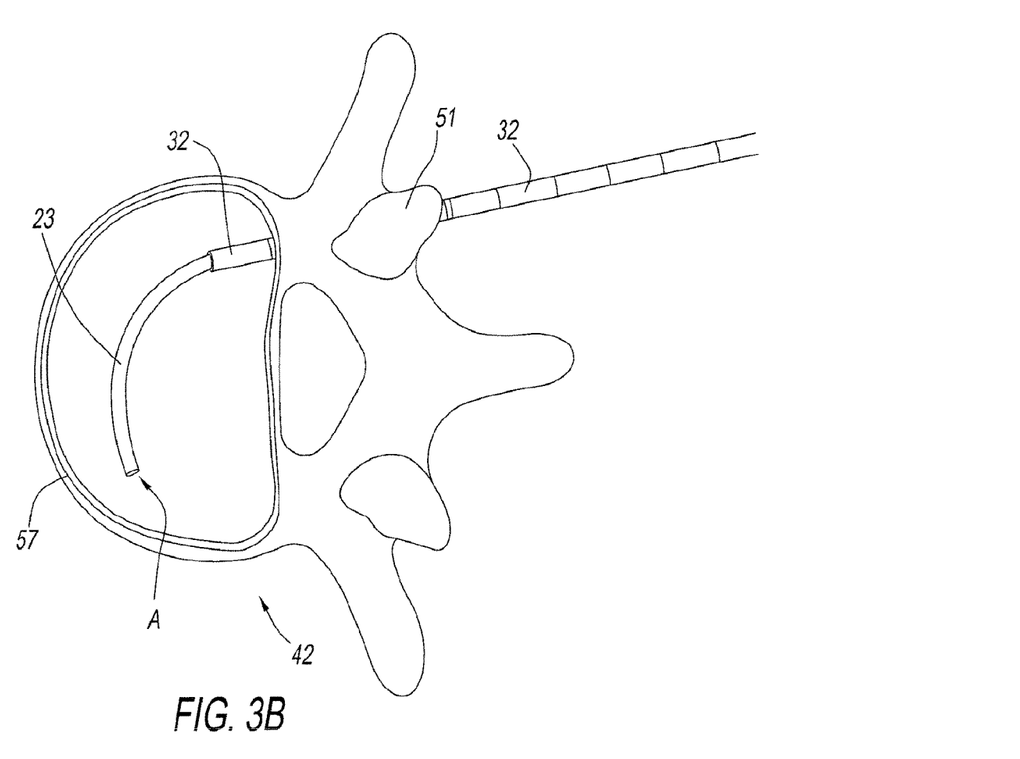
Figure 3C:
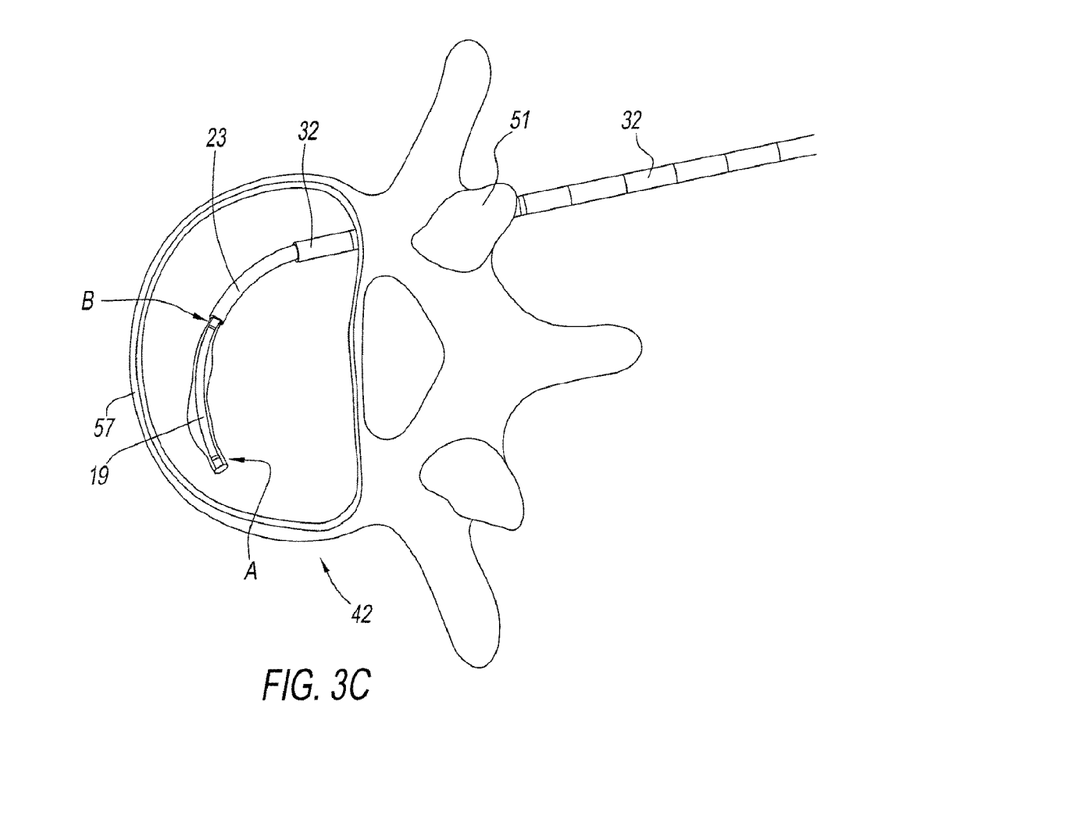
Figure 3D:
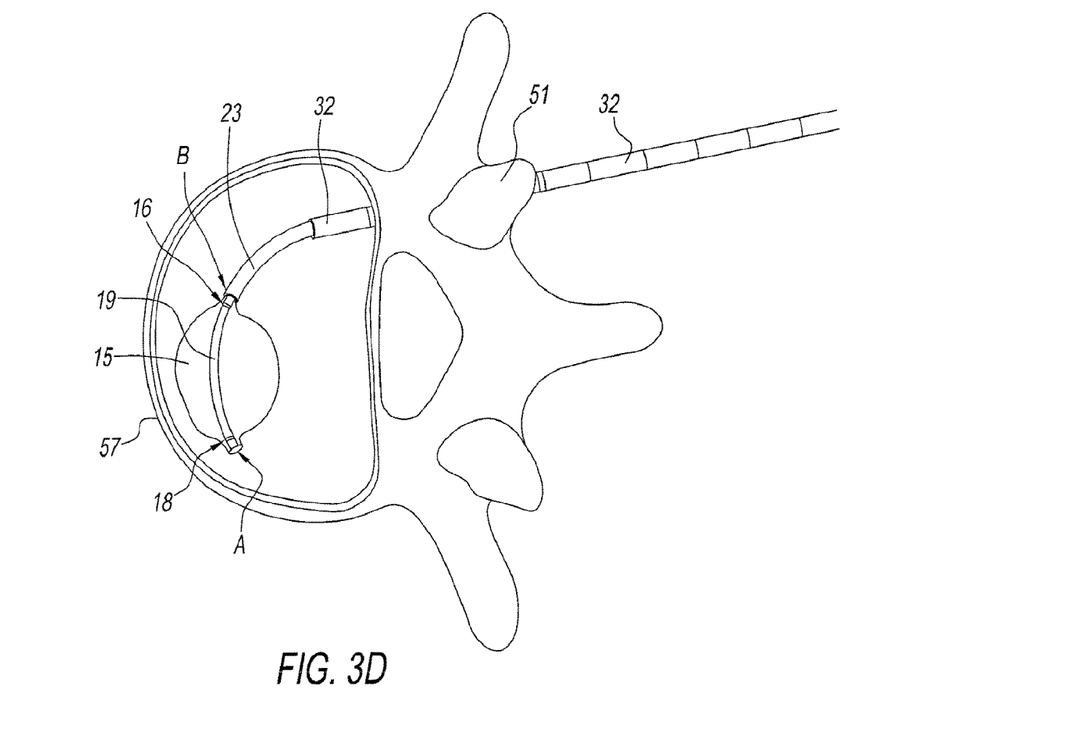
Figure 3E:
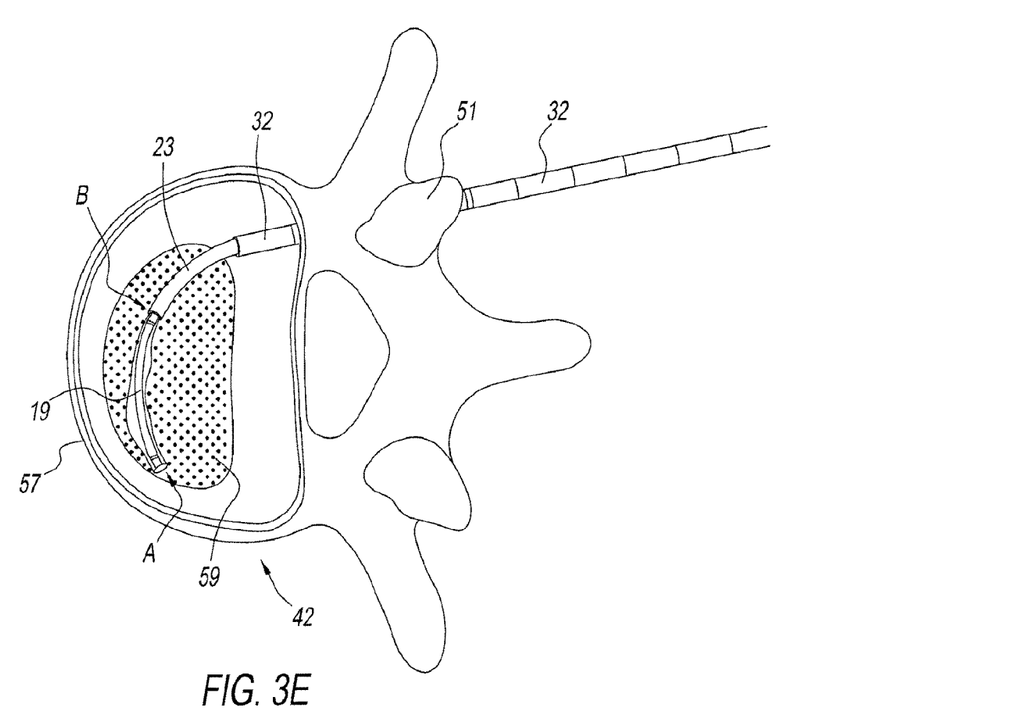
Figure 3F:
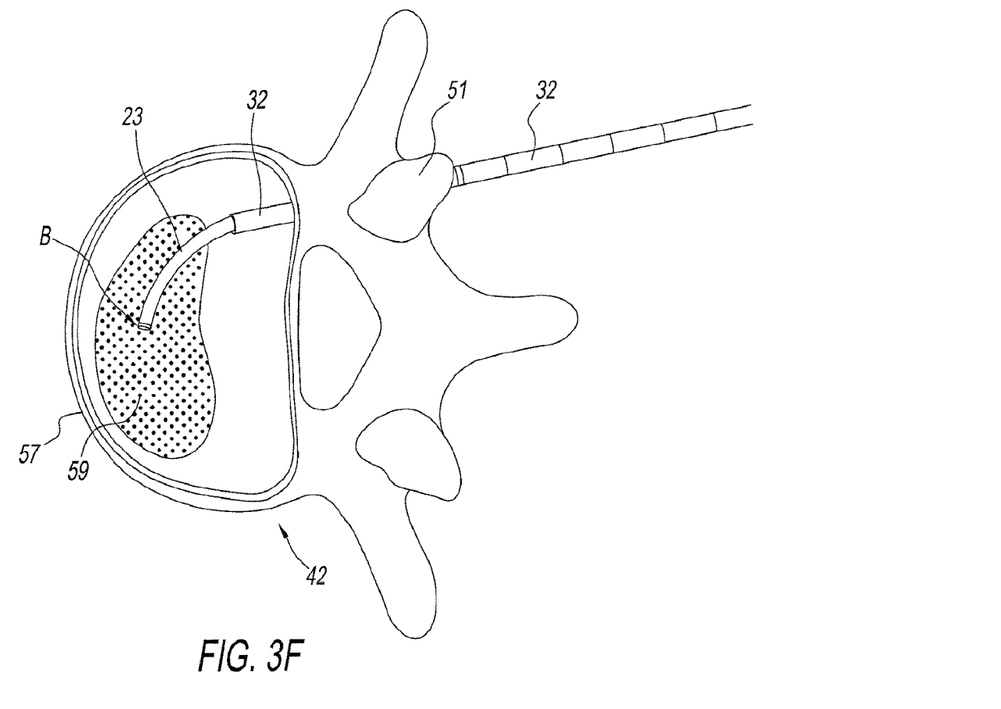
Figure 3G:
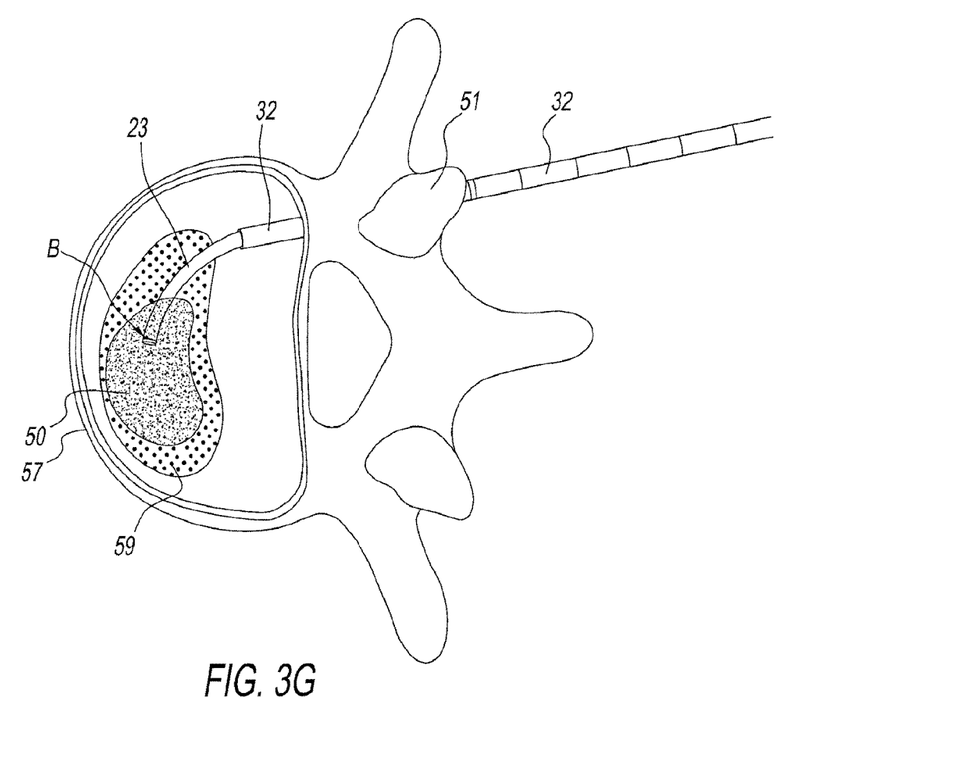
Figure 3H:
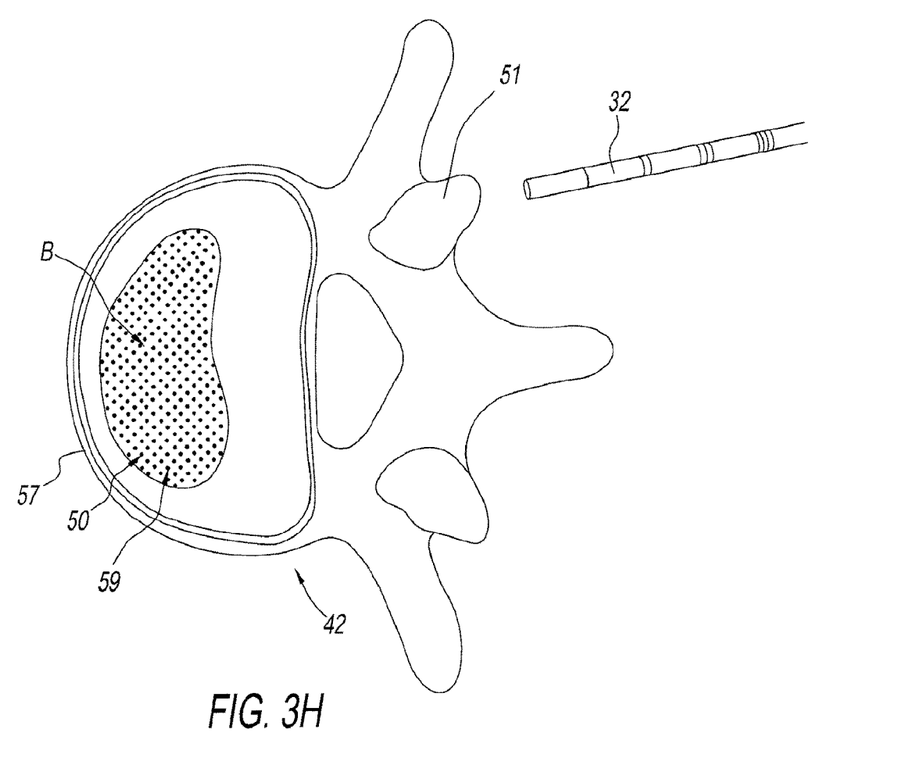

As shown in FIG. 3B, a needle assembly 1 may be inserted entirely through the length of the cannula 2, and the distal arcuate end 23 may be extended arcuately from the distal tip of the shaft 32 to a first position A within the portion of the vertebral body 42 comprised of cancellous bone, for example. Then, the needle 22 may be partially withdrawn such that the distal end 23 retreats to a second position B. The core 26 may be removed, and the inflatable bone tamp 11 may be inserted through the shaft of the needle 22 and into the channel within the cancellous bone previously cleared by the needle 22, until the distal end of the bone tamp is disposed between the first position A and the second position B, as illustrated in FIG. 3C, for example. A fluoroscope may be utilized to confirm the precise placement of the balloon 15, using the radiopaque markers 16, 18, before the balloon 15 is inflated as illustrated in FIG. 3D, for example, utilizing a digital inflation device attached to the inflation port 15 of the bone tamp 11. Then, as illustrated in FIG. 3E, the balloon 15 may be deflated, leaving a cavity or void 59 by way of displacement of the vertebral body and/or compaction of the cancellous bone. The bone tamp 11 may be removed without removing the needle 22, as illustrated in FIG. 3F, and a bone cement delivery device may be coupled to the needle to inject bone cement into the cavity or void 59, as illustrated in FIG. 3G, for example. When the proper amount of bone cement 50 is injected, the cavity or void 59 may be filled with bone cement, for example, as illustrated in FIG. 3H, and the needle 22 and catheter 2 may be withdrawn from the vertebral body 42. Once the bone cement hardens or cures, the vertebral body is stabilized and/or repositioned.

Figure 4A:
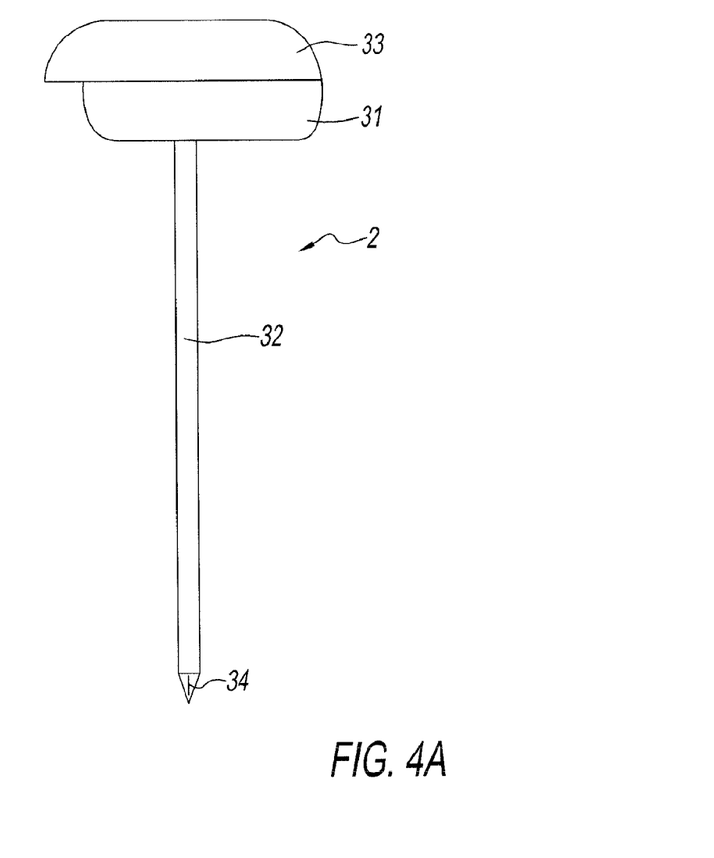
FIGS. 4A-4B illustrate an example of a cannula of a kyphoplasty device.
Figure 4B:
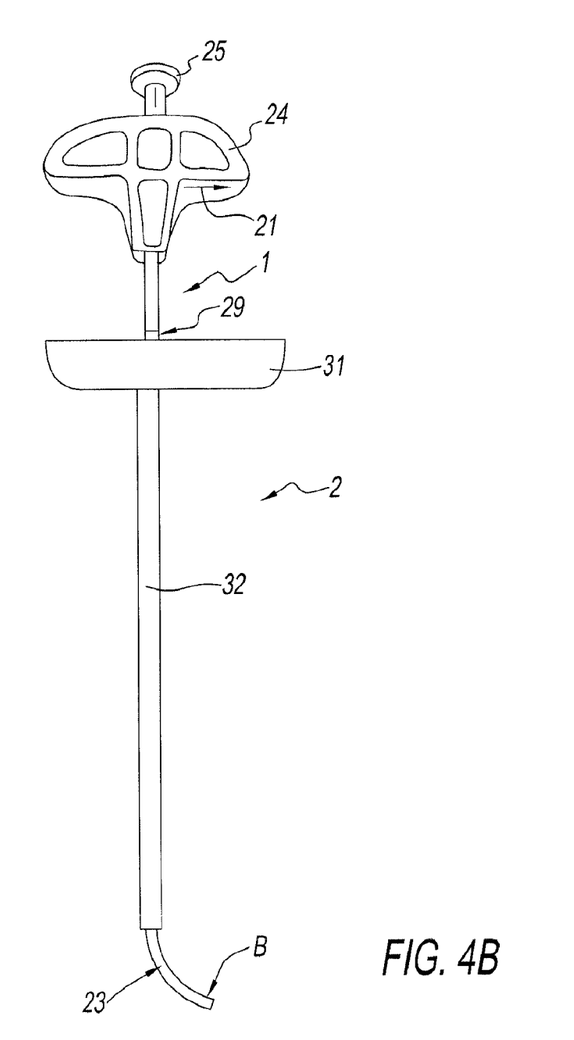

FIG. 4A illustrates an example of a cannula 2 having a stylet 34 extending from the shaft 32. A compound handle 31, 33 comprises a first handle portion 31 coupled to the shaft 32 and a second handle portion 33 coupled to the stylet 34. Thus, the stylet is removable and replaceable by a variety of stylets. In FIG. 4B, a needle assembly 1 is shown inserted through a cannula 2. This example shows how the witness mark 29 and directional indicator 21 may be utilized to determine the precise position B of the distal, arcuate end of the needle 22, for example. The same needle assembly 1 may be used for accessing the anterior portion of the vertebral body whether the cannula is inserted through the left pedicle 51 or the right pedicle 52, for example.

This detailed description provides examples including features and elements of the claims for the purpose of enabling a person having ordinary skill in the art to make and use the inventions recited in the claims. However, these examples are not intended to limit the scope of the claims, directly. Instead, the examples provide features and elements of the claims that, having been disclosed in these descriptions, claims and drawings, may be altered and combined in ways that are known in the art.

What is claimed is:

1. A kyphoplasty device comprises:
   an outermost cannula having a straight channel, the channel being of no greater than ten gauge, the channel being defined by a cylindrical wall, and the channel having a distal end at a length of at least thirty millimeters from a proximal end;
   an arcuate needle having a length at least ten millimeters longer than the length of the channel of the outermost cannula, and the needle having an arcuate end portion made of a material that has a flexibility and size selected such that the needle is insertable through the straight channel of the outermost cannula and the needle has a resiliency selected such that the arcuate end portion of the needle returns to an arcuate shape of the arcuate end portion upon exiting the channel of the outermost cannula; and an inflatable bone tamp having an outer diameter, when deflated, such that the bone tamp is insertable through the arcuate needle, while the arcuate needle is inside the outermost cannula, to a precise location where the bone tamp is needed to stabilize or reverse compression caused by vertebral collapse or fracture of vertebral bone structures, vertebral bone structures not being any portion of the device.

2. The device of claim 1, wherein the cannula is adapted to advance through hard bone of the vertebral bone structures.

3. The device of claim 2, wherein the material of the needle is of nitinol.

4. The device of claim 3, wherein a reservoir of bone cement and the needle are configured for coupling the reservoir with the needle for delivery of the bone cement contained in the reservoir through the needle, after the bone tamp is removed from the needle, such that the arcuate end of the needle delivers the bone cement precisely to a location of a cavity formed in the vertebral bone structures by the bone tamp, when the bone tamp is inserted through the needle and is inflated.

5. The device of claim 1, further comprising a diamond tip stylet inserted through the channel of the cannula.

6. The device of claim 5, further comprising a bevel tip stylet suitable for insertion through the channel of the cannula when the diamond tip stylet is removed from the channel of the cannula.

7. The device of claim 1, further comprising a bevel tip stylet inserted through the channel of the cannula.

8. The device of claim 1, wherein the cannula is adapted to fit through a pedicle of the vertebral bone structures, and the needle is adapted to access a region of the vertebral body near the cortical rim of the vertebral bone structures that is inaccessible to the cannula.

9. The device of claim 1, wherein the bone tamp has a thirteen gauge shaft and the bone tamp extends through the needle.

10. The device of claim 1, wherein two radiopaque markers are disposed at an interior portion of the bone tamp within the balloon to increase radiopacity under fluoroscopy.

11. The device of claim 1, further comprising a removable core, wherein the removable core is inserted through the needle during insertion of the needle through the cannula and into the vertebral bone structures, such that the removable core blocks any debris from clogging the needle.

12. A method of using the device of claim 1, comprising:
inserting a stylet through the cannula;
advancing the stylet and cannula through a pedicle of the vertebral bone structures to a location near a region of a cortical rim of the vertebral bone structures;
inserting the needle through the cannula such that the arcuate end portion extends into the region of the cortical rim that is otherwise inaccessible by the cannula;
inserting the inflatable bone tamp through the needle into the region of the cortical rim; inflating the bone tamp;
removing the bone tamp from the needle;
coupling a reservoir of bone cement to the needle;
injecting bone cement from the reservoir, through the needle, and into the region of the cortical rim.

13. The method of claim 12, wherein a removable core is removed from the needle after the needle is inserted into the region of the cortical rim and before inserting the inflatable bone tamp through the needle.

* * * * *